United States Patent [19]

Kingan et al.

[11] Patent Number: 5,344,821
[45] Date of Patent: Sep. 6, 1994

[54] PHEROMONOSTATIC PEPTIDE USED TO DISRUPT MATING OF THE CORN EARWORM, HELICOVERPA ZEA

[75] Inventors: Timothy G. Kingan, Catonsville; Ashok K. Raina, Beltsville, both of Md.

[73] Assignee: The United States of America, as represented by the Secretary of Agriculture, Washington, D.C.

[21] Appl. No.: 68,038

[22] Filed: May 28, 1993

[51] Int. Cl.$^5$ .................... A61K 37/02; C07K 7/10
[52] U.S. Cl. ........................................ 514/12; 530/324
[58] Field of Search ........................... 514/12; 500/524

[56] References Cited

U.S. PATENT DOCUMENTS

| | | | |
|---|---|---|---|
| 4,083,995 | 4/1978 | Mitchell et al. | 424/311 |
| 5,032,576 | 7/1991 | Raina et al. | 514/12 |
| 5,041,379 | 8/1991 | Fraser et al. | 405/69.1 X |

OTHER PUBLICATIONS

J. Exp. Biol. 183, 61–76 (1993), Kingan et al.
Bodnar et al., Abst. of Ann. Mtg. of Society for Microbiologists (1992).
Kingan et al., Soc. Neurosci. Abstr. vol. 17 p. 549 (1991).
Sparks et al., Southern Cooperative Series Bulletin pp. 50–65 (1988).
Sekul et al., Journal of Economic Entomology, vol. 68(5) pp. 603–604 (1975).

*Primary Examiner*—Howard E. Schain
*Attorney, Agent, or Firm*—Janelle S. Graeter

[57] ABSTRACT

A polypeptide having the property of rendering a female *Helicoverpa zea* moth non-receptive to mating was isolated from the reproductive tract of the male moth. The peptide is transferred from the male to the female during mating and causes a depletion of the female sex pheromone thereby resulting in a decline in sexual attractiveness for at least 24 hours.

The peptide is referred to as pheromonostatic peptide, or PSP. It is a basic peptide having 57 amino acid residues, a molecular weight of 6617 daltons and contains one pair of cysteine residues in a disulfide linkage.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 57 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Helicoverpa zea ( i x ) FEATURE:
( A ) NAME/KEY: Modified-site
( B ) LOCATION: 1

( i x ) FEATURE:
( A ) NAME/KEY: Modified-site
( B ) LOCATION: 6

( i x ) FEATURE:
( A ) NAME/KEY: Disulfide-bond
( B ) LOCATION: 42..54

( x i ) SEQUENCE DESCRIPTION: SEQ ID NO:1:

```
Xaa Ile Ile Asn Asn Xaa Asp Tyr His Asp Asp His His Gly Asp Gln
1               5                   10                  15

Pro Thr Leu Leu Leu Arg Ser Gln Pro Glu Arg Met Arg Pro Leu Leu
            20                  25                  30
```

Leu Ala Arg Asp Ala Phe Gly Gly Glu Cys Pro Pro Ser Ser Phe His
       35              40                    45

Lys Leu Lys Asn Trp Cys His Ile Val
       50              55

PHEROMONOSTATIC PEPTIDE USED TO DISRUPT MATING OF THE CORN EARWORM, HELICOVERPA ZEA

BACKGROUND OF THE INVENTION

1. Field of the Invention

This invention relates to a polypeptide which is transferred from the male corn earworm moth to the female during mating. After transfer, a decline in the production of sex pheromone is observed for at least 24 hours and the female becomes unattractive to males over that period of time. A continued presence of this peptide within the female serves as an effective means of insect control by rendering it permanently unattractive. The peptide is also useful in the study of insect physiology.

2. Description of the Prior Art

Insect infestation of crops is a primary cause of crop loss throughout the United States. A wide variety of chemical pesticides has been relied upon in the past to control insect pests; however, environmental concerns as well as consumer safety have led to the deregistration of many pesticides and a reluctance to use others on agricultural products which are ultimately consumed as food. As a consequence, scientists have begun to pursue the development of biological control agents which are environmentally safe both from a consumer and an agricultural point of view.

The corn earworm *Helicoverpa zea* (*H. zea*), formerly *Heliothis*, causes an estimated $1.2 billion in crop damage each year, therefore scientists have been exploring biocontrol methods effective for this pest.

A number of individuals have sought to exploit the natural sex attractants of insects to disrupt reproductive behavior.

Sekul et al. (*J. Econ. Entomology*, 1975) identified Z-11-hexadecenal, produced and released by the adult female of H. zea, and referred to the compound as a sex attractant inhibitor. The compound elicited strong sex stimulation activity in caged males; however, in field experiments, the catch of males in sticky or electric grid traps was inhibited in the presence of the compound.

Mitchell et al. (U.S. Pat. No. 4,083,995, 1978) disclosed a chemical of non-biological origin, (Z)-9-tetradecen-1-ol formate [(Z)-9-TDF], which was effective in reducing mating in corn earworm and tobacco budworm moths.

Sparks et al. (Southern Cooperative Series Bulletin, 1988) discussed *Heliothis* pheromones and their potential use as biocontrol agents by mating disruption.

Raina et al. (U.S. Pat. No. 5,032,567, 1991) disclosed a neuropeptide referred to as Hez-PBAN, which was isolated from H. zea females. The peptide activates pheromone biosynthesis in the moth; therefore appropriate application of this peptide may lead to the production of pheromone at inappropriate times or in inappropriate amounts, thereby upsetting the normal reproductive cycle. In addition, melanization in the larvae is also activated by Hez-PBAN, and significant mortality associated with melanization was observed in inoculated larvae.

Kingan et al. (*Soc. Neurosci.* Abstract 17:549, 1991) reported the discovery of pheromonostatic factors (PSFs) from accessory glands of male H. zea moths and discussed preliminary studies using accessory gland extracts.

Fraser et al. (U.S. Pat. No. 5,041,379, 1991) described Heliothis expression systems useful for the production of vaccines, antigens for immunoassay procedures, insecticides and foreign peptides or proteins. Heterologous genes controlled by a Heliothis polyhedrin promoter were inserted into a baculovirus vector for introduction into an appropriate host system for expression of the foreign DNA.

SUMMARY OF THE INVENTION

It is an object of the invention to provide a novel polypeptide obtained from male *Helicoverpa* which, upon injection or ingestion into the female *Helicoverpa*, renders the female unattractive to male insects. Effective analogs or derivatives of the peptide are also contemplated.

It is also an object of the invention to provide a method of controlling H. zea infestation utilizing the novel polypeptide in an agriculturally acceptable carrier.

DETAILED DESCRIPTION OF THE INVENTION

Insects are noted for their broad exploitation of volatile chemicals as environmental or physiological cues in eliciting a number of behaviors necessary for survival and reproduction. In the noctuid moth H. zea, as in many other species of moths, mating is facilitated by a pheromone biosynthetic activating neuropeptide (PBAN) that stimulates production and release of species-specific sex pheromones by the female (Raina et al, supra). When a sufficient level of pheromone has accumulated in the pheromone gland, the female begins her "calling" behavior in which she extrudes her ovipositor and fans her wings to disperse the pheromone. The receptive female will then accept a mate if he attempts copulation. As a result of mating, production and release of pheromone decreases dramatically, and the female becomes unreceptive to the copulatory attempts of pheromone-primed males.

Non-volatile chemicals may also trigger behavioral changes. As described above, the neuropeptide PBAN initiates pheromone biosynthesis. In addition, another polypeptide, pheromonostatic peptide (PSP) is produced in the reproductive tract of male H. zea and is transferred with spermatozoa to the female during mating. Upon transfer, this polypeptide causes a depletion of the sex pheromone used for the attraction of potential mates, thus assuring that a second male will not be attracted to the female. The phenomenon has been observed to last at least 24 hours.

The polypeptide was extracted from the accessory glands and duplex (storage organ for seminal fluids and spermatozoa) which were removed under saline from the male's abdomen. Following extraction, the material was purified by high performance liquid chromatography (HPLC). Two pure peptides were obtained, their retention times in HPLC differing by about 3 minutes. The two peptides were determined by mass spectrometry to have identical molecular weights.

The activity of the two peptides was evaluated by bioassay. Females were first ligated between head & thorax to remove their own source of PBAN; they were then injected with PBAN to stimulate pheromone biosynthesis, followed by a later injection with the isolated material. It was found that females receiving no PSP typically accumulated pheromone in much higher amounts than those having been injected with PSP.

PSP has now been isolated and identified. It has been shown to be a basic, 57-amino acid peptide with a molecular weight of 6615 daltons, and it contains one pair of cysteine residues in a disulfide linkage.

The amino acid sequence (Seq ID No:1) of the later-eluting of the two polypeptides was determined. Sequence analysis was carried out by a combination of microcapillary HPLC/electrospray ionization tandem mass spectrometry, Edman degradation, and amino acid analysis. The molecule contains a blocked amino-terminus (pyro-Glu), a mixture of asparagine and aspartic acid at position 6, a disulfide bond between cysteine-42 and cysteine-54, and an amidated carboxy terminus. The amino acid sequence is shown below:

(SEQ ID No:1)

```
X—ILE—ILE—ASN—ASN—Y—ASP—TYR—HIS—ASP—ASP—
HIS—HIS—GLY—ASP—GLN—PRO—THR—LEU—LEU—LEU—
ARG—SER—GLN—PRO—GLU—ARG—MET—ARG—PRO—LEU—
LEU—LEU—ALA—ARG—ASP—ALA—PHE—GLY—GLY—GLU—
CYS—PRO—PRO—SER—SER—PHE—HIS—LYS—LEU—LYS
     \
      S
       \
        S
         \
ASN—TRP—CYS—HIS—ILE—VAL—NH2,
``` where X is pyro-GLU and Y is a mixture of ASN and ASP.

In order for the peptide to be effective, it must be internalized, and this may be accomplished by injection or ingestion. Although injection is a highly effective technique, for all practical purposes its use is limited to small-scale situations such as research and development. Not all moths feed prior to mating; however, *H. zea* and other noctuids generally do. Ingested PBAN is known to evoke a physiological response typical of that of an injected moth, therefore feeding lures or feeding attractants laced with PSP and placed or sprayed in an infested area is an attractive means of administration.

The nucleic acid sequence which codes for the novel polypeptide may be incorporated into a vector system and applied to infested areas as another means of administration. Insect-specific viruses such as baculoviruses provide an effective means of infecting target pests with foreign heterologous genes which can be expressed in the host. Baculovirus vector systems are well-known in the art, and their use is described by B.D. Hammock et al. [*Archives of Insect* Biochemistry and Physiology, 22:314-344 (1993)] and Fraser et al., supra, both references herein incorporated by reference. Essentially, the DNA sequences which encode the desired polypeptide are inserted into the baculovirus genome. The sequences are under the control of an appropriate promoter, such as the Heliothis polyhedrin promoter, which directs the expression of the foreign genes.

In a preferred embodiment, the gene is expressed in the form of a recombinant occlusion body, which consists of a multimeric protein in the form of a paracrystalline lattice around the virion. Upon ingestion, the crystalline occlusion body in which the recombinant virion is embedded dissolves in the high pH typical of the insect gut, releasing infective virions. Insect cells then take up the virus particles and begin producing the protein encoded by its genetic material, in this case PSP. PSP is then released into the female's blood, causing depletion of the sex pheromone and thereby rendering the female unattractive to males and ensuring that mating does not occur.

Both the peptides and the recombinant occlusion bodies may be administered with an agriculturally acceptable carrier either topically or orally, such as with the feeding lures and/or the feeding attractants previously mentioned.

The peptides and the recombinant occlusion bodies are each effective when applied separately. In order to enhance infectivity, however, they may also be applied in combination. Effective dosages will vary with the particular conditions, amount of infestation and duration of treatment. Suggested amounts are in the range of 3-1000 pmoles.

Feeding lures and attractants include host plant volatiles which attract females for feeding and as sites for laying eggs. Also useful are sucrose or other sugar solutions.

While the peptide may be obtained by the isolation procedure described by the Examples, conventional chemical synthesis is also contemplated as an effective means of providing the peptide.

The following examples are intended only to further illustrate the invention and are not intended to limit the scope of the invention as defined by the claims.

EXAMPLES

Example 1—Isolation of PSP

The accessory glands and duplex are removed under saline from the abdomen of approximately 1000 male moths and placed in a tube held in dry ice.

After dissection, the glandular tissue is extracted with a polytron (Brinkmann Instruments, Westbury, NY) in a 20-fold excess (wt/vol) of aqueous acids including 1N HCl, 5% formic acid, 1% trifluoroacetic acid (TFA), and 0.1 M NaCl. The extract is centrifuged at 13,000×g for 15 minutes, then decanted through cheesecloth to remove fatty material that will not pellet with centrifugation.

The clarified extract is desalted by absorption to C18 reverse phase resin in Sep-Pac cartridges (Millipore Corp., Milford, MA), washing with 20 mM ammonium acetate, pH 5.0, and eluting proteins and peptides with 40% acetonitrile in 20 mM ammonium acetate.

The eluted material is diluted with an equal volume of distilled water and absorbed to a cartridge containing a cation exchange resin (Accell CM, Millipore Corp., Milford, MA) which had previously been rinsed with 20 ml ammonium acetate containing 1M NaCl followed by ammonium acetate alone. After applying the sample, the cartridge is rinsed with 10 ml ammonium acetate containing 50 mM NaCl; the original unretained material and the material eluting with ammonium acetate containing 50 mM NaCl are discarded. The cartridge is then rinsed with ammonium acetate containing 0.5M NaCl. This material is then desalted on a C18 Sep-Pak cartridge as described supra, except that peptide is eluted with 40% acetonitrile containing 0.1% TFA instead of ammonium acetate. The eluate is reduced in volume by about one-half by vacuum centrifugation. The material may be evaluated at this point by bioassay for use as a biocontrol agent, or it may be further purified.

For further purification, the material is applied to a C4 reverse phase HPLC column in 0.1% TFA containing 10% 2-propanol. A gradient of propanol is developed at 0.5%/min with a flow-rate of 0.4 ml/min. Active material is contained in 4 adjacent 1 min fractions of UV-absorbing material late in the chromatogram, after the bulk of the absorbing material is eluted. This material is pooled and dried by vacuum centrifugation.

The resulting white powder is dissolved in 20 mM sodium phosphate, pH 3.0, containing 30% acetonitrile. It is then loaded onto a cation-exchange HPLC column (sulfopropyl functional group; SP-5-PW, Biorad Inc., Richmond, CA) while pumping the same solvent. A gradient of NaCl is then developed, increasing from 0 at the rate of 10 mM/min, while pumping solvent at 1 ml/min. Aliquots of individual fractions are prepared, neutralized with 0.1N NaOH, and dried by vacuum centrifugation. The resulting white powder is dissolved in distilled water for bioassay purposes. Active material is found in fractions eluting with 0.25–0.35M NaCl. Active fractions are reduced in volume by about one-half by vacuum centrifugation and pooled.

For further purification, active fractions are loaded onto a wide-pore C8 reverse phase column (4.6 mm diameter) while pumping 50 mM sodium phosphate, pH 6.0, containing 20% acetonitrile. A gradient of acetonitrile is then developed at 0.67%/min with a flow rate of 0.7 ml/min. Active material elutes in two narrow zones late in the chromatogram. Active fractions are reduced in volume by about one-half by vacuum centrifugation.

The two zones of active material are chromatographed separately in a reverse phase column identical to the preceding step, except that its internal diameter is 2.1 mm. The solvent used is acetonitrile in 0.1% TFA, and the gradient develops from 20% acetonitrile at the rate of 0.67%/min with a flow rate of 0.2 ml/min. Two pure peptides are obtained, their retention times differing by about 3 min.

Example 2—Bioassay

Females in their 1st or 2nd photophase after emergence are ligated between the head and thorax with silk thread. The following morning, approximately 16 hours later, the females are injected with 2 picomoles of the pheromonotropic peptide PBAN. One hour later, they are injected a second time with fractionated material obtained as described supra. Two hours later, the tip of the abdomen (at the 7th abdominal segment), containing the ovipositor and the glandular tissue producing sex pheromone, is excised and extracted with 5–15 μl heptane The amount of the major component of sex pheromone, Z-11-hexadecenal, is quantified by gas chromatography. Females receiving saline (control) at the second injection typically contain 50–150 nanograms pheromone in the extract while females having been injected with the peptides extracted from the male reproductive tract are found to have 1–5 nanograms.

We claim:

1. An isolated polypeptide comprising the amino acid sequence:

(SEQ ID No:1)

X—ILE—ILE—ASN—ASN—Y—ASP—TYR—HIS—ASP—

ASP—HIS—HIS—GLY—ASP—GLN—PRO—

THR—LEU—LEU—LEU—

ARG—SER—GLN—PRO—GLU—ARG—MET—ARG—

PRO—LEU—

LEU—LEU—ALA—ARG—ASP—ALA—PHE—GLY—

GLY—GLU

CYS—PRO—PRO—SER—SER—PHE—HIS—LYS—LEU—LYS
   \
    S
     \
      S
       \
ASN—TRP—CYS—HIS—ILE—VAL—NH$_2$, where X is pyro-GLU and Y is a mixture of ASN and ASP, and effective analogs and derivatives thereof.

2. The polypeptide of claim 1 in an agriculturally acceptable carrier.

3. A method of controlling *Helicoverpa zea* by administering effective amounts of the polypeptide of claim 1 to infested areas.

* * * * *